(12) United States Patent
Luborsky

(10) Patent No.: US 6,458,550 B1
(45) Date of Patent: Oct. 1, 2002

(54) TEST FOR OVARIAN AUTOIMMUNITY BY DETECTING AUTOANTIBODIES TO CYP17

(75) Inventor: Judith L. Luborsky, Chicago, IL (US)

(73) Assignee: Rush-Presbyterian-St. Luke's Medical Center, Chicago, IL (US)

( * ) Notice: Subject to any disclaimer, the term of this patent is extended or adjusted under 35 U.S.C. 154(b) by 0 days.

(21) Appl. No.: 09/479,234

(22) Filed: Jan. 7, 2000

(51) Int. Cl.$^7$ ............... G01N 33/573; G01N 33/564; G01N 33/567; G01N 33/543

(52) U.S. Cl. ............ 435/7.4; 435/7.1; 435/7.92; 435/7.93; 435/7.95; 436/503; 436/506; 436/518; 600/551

(58) Field of Search ............... 435/7.1, 7.21, 435/7.4, 7.92, 7.95, 18, 195, 7.94; 436/503, 506, 811, 518; 600/33, 551

(56) References Cited

U.S. PATENT DOCUMENTS 5,376,533 A * 12/1994 Maclaren et al. ............ 435/7.4
5,705,400 A * 1/1998 Furmaniak-Wehr ......... 435/7.4

OTHER PUBLICATIONS

Krohn et al., 1992. Identification by molecular cloning of an autoantigen associated with Addison's disease as steroid 17alpha–hydroxylase. Lancet 339: 770–773, Mar. 1993.*
Peterson et al., 1994. Mapping of B cell epitopes on steroid 17alpha–hydroxylase, an autoantigen in autoimmune polyglanular syndrome type I. Clin. Exp. Immunol. 98: 104–109, 1994.*
Betterle, C. et al., "Adrenal and ovarian autoimmunity," *European Journal of Endocrinology*, vol. 138, pp. 16–25, 1998, published by the Society of the European Journal of Endrocrinology.
Betterle, C. et al., "Adrenal–Cortex Autoantibodies and Steroid–Producing Cells Autoantibodies in Patients with Addison's Disease: Immunoprecipitation Assays," *Journal of Clinical Endocrinology and Metabolism*, vol. 84, No. 2, pp. 618–622, 1999, published by The Endocrine Society.
Arif et al., *J. Clin. Endocrinol. Metab* 81(12): 4439–4445 (1996).
Belloc et al., *Pharmacogenetics* 7: 181–186 (1997).
Briere et al., *J. Histochem. Cytochem.* 45(10): 1409–1416 (1997).
Buczko et al., *J. Steroid Biochem. Molec. Biol.* 52(3): 209–218 (1995).
Chen et al., *J. Clin. Endocrinol. Metab.* 81(5): 1871–1876 (1996).
Chu et al., *Endocrinology* 140(2): 632–640 (1999).
Degtyarenko et al., *FEBS Lett.* 332(1,2): 1–8 (1993).
Dufau et al., *Steroids* 62: 128–132 (1997).
Farhi et al., *Human Reprod.* 12(2): 241–243 (1997).
Hoek et al., *Endocrin. Rev.* 18(1): 107–134 (1997).
Katulski et al., *Endocrinol. Invest.* 21:304–309 (1998).
Lewis et al., *J. Steroid Biochem. Mol. Biol.* 66(4): 217–233 (1998).
Luborsky et al., *J. Clin. Endocrinol. Metab.* 70(1): 69–75 (1990).
Luborsky et al., *Clinical Immunol.* 90(3): 368–374 (1999).
Luborsky et al., *J. Reprod. Immunol.* 42: 79–84 (1999).
Lund et al., *Endocrin. Res.* 24(3&4): 497–504 (1998).
MacCorkle et al., *Anti Ovary Antibody Elisa Kit*, Submitted to ASRM Meeting (1999).
Meyer et al., *Obstet. Gynecol.* 75(5): 795–799 (1990).
Nedelcheva–Kristensen et al., *Cancer Res.* 59:2825–2828 (1999).
Roitt, Essential Immunology, Eighth Edition 19: 383–428 (1994).
Tung et al., *Human Reproduction Update* 1(1): 35–50 (1995).

* cited by examiner

*Primary Examiner*—Christopher L. Chin
*Assistant Examiner*—James L. Grun
(74) *Attorney, Agent, or Firm*—Foley & Lardner

(57) ABSTRACT

Ovarian autoimmunity is implicated in ovarian dysfunction associated with premature ovarian failure (POF) and unexplained infertility. A rapid, quantitative, and inexpensive method of clinical diagnosis of ovarian autoimmunity is provided. Diagnosis is provided by detection of autoantibodies that react with an ovarian antigen, 17 -alpha-hydroxylase. This diagnostic method is applicable to ovarian autoimmunity unassociated with polyglandular disease.

9 Claims, 1 Drawing Sheet

TEST FOR OVARIAN AUTOIMMUNITY BY DETECTING AUTOANTIBODIES TO CYP17

BACKGROUND OF THE INVENTION

Premature ovarian failure (POF), also know as premature menopause, is defined as the secondary loss of ovarian function before the age of 40 years. POF affects about 1.3 million women in the United States alone. Coulam et al. (1983), Luborsky et al. (1999a). Known contributing factors include irradiation, chemotherapy, and chromosomal abnormalities, although many cases of POF have an unknown origin (idiopathic POF).

Evidence has accumulated that the ovary is a target of an autoimmune process in women with idiopathic POF. Evidence for an autoimmune etiology includes the frequent association of POF with other autoimmune disorders, lymphocytic infiltration of the ovaries, and ovarian autoantibodies in serum. About half of all women with POF express ovarian autoantibodies. Luborsky et al. (1999a).

Ovarian autoantibodies also are detected in sera of women with unexplained infertility. Women with unexplained infertility represent about 15–20% of all infertility cases (about 2% of the population). Forti et al. (1998). Unexplained infertility is defined as the inability to conceive for at least one year, despite normal results on standard tests for reproductive function, which include semen analysis, postcoital testing, ovulation, and tubal patency. Like women with POF, about half of women with unexplained infertility express ovarian autoantibodies. POF may manifest itself initially as unexplained infertility. Farhi et al. (1997).

Autoimmune disorders, in general, are associated with an aberrant immune response against endogenous antigenic determinants, although it is often unclear whether the presence of autoantibodies represents the cause or the effect of cellular pathology. Although the mechanisms underlying ovarian autoimmunity are not completely understood, ovarian autoantibodies presumably are elicited by inappropriate exposure of the immune system to endogenous ovarian proteins. Tung et al. (1995a), Tung (1995b).

The primary diagnostic indicator for an autoimmune disease is the presence of an autoantibody that is directed against a specific endogenous target, or autoantigen, and that is correlated with characteristic clinical features. However, polyclonal activation may occur during the course of the autoimmune reaction, resulting in increased autoantibody titers to a variety of autoantigens. Roitt (1994). For example, in thyroid autoimmunity, there are at least two diagnostically useful autoantigens, peroxidase and thyroglobulin. Thus, while there is a there is a desire to find a specific autoantibody that is a primary diagnostic indicator for POF and unexplained infertility, there is an expectation that multiple autoantigens will be associated with these conditions. Luborsky et al. (1999a).

Diagnosis of Ovarian Autoimmunity, Idiopathic POF, and Unexplained Infertility

Ovarian autoimmunity may be present 8–10 years before the manifestation of clinical symptoms. Thus, premature menopause and unexplained infertility may represent the endpoint of a slow, degenerative process with subclinical intermediate symptoms. Farhi et al. (1997). Accordingly, early diagnosis of autoimmune disease allows treatment to maintain or restore ovarian function before a clinical manifestation of infertility or POF.

Unfortunately, diagnosis of ovarian autoimmunity has presented significant problems. Current methods of assessing ovarian function rely on evaluation of the pattern and length of menstrual cycles, and measurement of estradiol and follicle stimulating hormone (FSH) levels in serum during the early follicular phase. Menstrual cycle evaluation is subjective and is generally indicative only of the final clinical manifestations of ovarian failure. Measurement of serum endocrine levels does not differentiate between endocrine or autoimmune etiologies for ovarian dysfunction. Luborsky et al. (1999b), Luborsky et al. (1998).

Recently, it has been possible to diagnose ovarian autoimmunity by detecting the presence of ovarian autoantibodies. The presence of ovarian autoantibodies is correlated with poor estradiol production in response to hormone therapy and with poor pregnancy outcome following in vitro fertilization (IVF). Luborsky et al. (1999a), Meyer et al. (1990), Gobert et al. (1992), Barbarino-Monnier et al. (1991). In contrast, presence of ovarian autoantibodies does not correlate with FSH levels, indicating that detection of ovarian autoantibodies provides an assessment of ovarian failure independent of routine endocrine assessment. Luborsky et al. (1999b), Luborsky et al. (1998). The presence of ovarian autoantibodies is highly correlated with POF and unexplained infertility, but not other categories of infertility. McKenna et al. (1999), Luborsky et al. (1999c). Thus, detection of ovarian autoantibodies provides a reliable indicator of an ongoing ovarian disease.

Methods of Detecting Ovarian Autoantibodies

Previously, the only method of detecting ovarian autoantibodies was immunohistochemistry, which is subjective, labor intensive, and qualitative. Immunohistochemistry necessitates the use of thin sections of ovarian tissue. Since there are rarely more than a few active follicles expressing antigens of possible relevance to fertility in the whole ovary, the variability from section to section is extremely high.

Recently, however, it has been possible to screen sera for ovarian autoantibodies using an enzyme-linked immunosorbent assay (ELISA). Luborsky et al. (1990), MacCorkle et al. (1999). In this assay, human sera are contacted with immobilized ovarian antigens. Autoantibodies against ovarian antigens are detected by the formation of immune complexes with the immobilized antigens. The ease and feasibility of using this assay is increased by the recognition that rat ovarian tissue can be used as a source for antigens to identify ovarian autoantibodies (correlation greater than 95%). Thus, at least one major antigenic determinant in ovarian tissue is structurally conserved between rat and human antibodies, such that the human ovarian autoantibodies are capable of reacting with rat antigen(s). This ELISA can be used in conjunction with standard reproductive endocrine level tests to diagnose or predict POF or unexplained infertility. The ELISA further can be used to measure the progress of treatment of POF or unexplained infertility, by such methods as immunosuppression with glucocorticosteroids. Luborsky et al. (1990), Hoek et al. (1997). As one alternative to immunosuppressive therapy, individuals positive for ovarian autoantibodies may choose to bear children sooner, before it becomes difficult or impossible due to loss of ovarian function.

Identification of an Antigen Associated with an Ovarian Autoimmune Etiology for Infertility Little is known of the identity of the ovarian determinants that interact with human autoantibodies. One line of evidence suggests that ovarian antigens may be diverse. Immunohistochemical staining of rat ovarian tissue sections indicates antigenic determinants in the nucleus, cell membrane, and cytoplasmic organelles, suggesting multiple antibody specificities in autoimmune sera. Meyer et al. (1990).

The identification of a determinant that is unique to ovarian autoimmunity would have significant predictive and diagnostic value. Once identified, an antigen could be isolated, thus providing an inexpensive and standardized source of an antigen for diagnostic screens. A diagnostic procedure, based on detection of such an antigen, could identify individuals at risk of POF or unexplained infertility before the onset of ovarian dysfunction. Alternately, such a diagnostic procedure could permit evaluation of the progress of therapy to treat or reverse ovarian dysfunction.

Two endocrine glands synthesize steroid hormones, the ovary and the adrenal. Steroid-producing cells (SPCs) produce steroids in both of these glands. SPCs in the two glands utilize partially overlapping sets of metabolic enzymes to produce different steroid hormones. Both glands express the P450 side chain cleavage enzyme (P450 scc) in an initial step in steroid hormone biosynthesis. However, 21-hydroxylase (21-OH) is expressed abundantly in the adrenal but not in the ovary. By contrast, 17-alpha hydroxylase (17-OH), in humans, is expressed at high levels in the ovary but not in the adrenal. Dufau et al. (1997).

Autoantibodies against the SPC antigens 17-OH, P450 scc, and 21-OH have been found in sera of patients with POF associated with autoimmune adrenal disease (polyglandular disease), but not in sera of POF patients without polyglandular disease. Chen et al. (1996). Autoantibodies that recognize these SPC antigens were detected by the formation of immune complexes with radiolabeled enzymes that were prepared by in vitro transcription. Autoantibodies against these SPC antigens were detected in patients with type I or type II polyglandular syndrome (APS), adrenal cortex antibody (ACA), and Addison's disease (adrenal insufficiency). Significantly, no antibodies to 17-OH, P450 scc, or 21-OH were found in POF patients without adrenal autoimmunity, except for one serum containing low levels of anti-17-OH antibodies. Thus, it would appear from this data that these autoantibodies are associated with an adrenal etiology in polyglandular syndrome but not with an ovarian etiology in POF and unexplained infertility.

Thus, there is an ongoing need to identify autoantibodies associated with an ovarian etiology in POF and unexplained infertility. This is especially important because Addison's disease is relatively rare, and POF associated with adrenal autoimmunity accounts for only about 2–10% all cases of idiopathic POF. Hoek et al. (1997).

Only limited progress has been made in finding an antigen specifically associated with idiopathic POF that occurs in the absence of polyglandular diseases. Potentially, one such antigen is 3 beta-hydroxysteroid dehydrogenase (3 beta HSD), another enzyme involved in steroid metabolism. Arif et al. (1996). Although autoantibodies against 3 beta HSD apparently are associated with idiopathic POF occurring in the absence of polyglandular disease, these autoantibodies appear in only 10 of 48 (21%) POF sera. Not only does 3 beta HSD appear with a low frequency in POF sera, but this enzyme is also present in adrenal tissue. Thus, the presence of 3 beta HSD autoantibodies is a relatively poor indicator of an ovarian etiology in autoimmune infertility.

Thus, there is a current need in the art to define a specific antigen that is diagnostic for a majority of POF patients with ovarian autoimmunity that occurs in the absence of polyglandular disease.

SUMMARY OF THE INVENTION

Autoantibodies to a CYP17 protein (17-alpha-hydroxylase, or 17-OH) are found in a majority of sera from patients with unexplained infertility and POF, as described herein. It has been discovered that anti-CYP17 autoantibodies are indicative of an ovarian etiology of POF that is unassociated with polyglandular disease. This strong correlation between anti-CYP17 autoantibodies and ovarian autoimmunity allows a quick and efficient diagnosis of ovarian autoimmunity by detecting the presence of this autoantibody in a sample from a test subject.

Accordingly, the invention provides a method of diagnosing an ovarian autoimmune etiology of unexplained infertility or POF, comprising contacting a biological sample, preferably serum, from a patient and detecting an anti-CYP17 autoantibody, preferably through detecting the formation of an immune complex between the autoantibody and CYP17. In one embodiment, the method is applied to women manifesting POF or unexplained infertility, or suspected of manifesting either, in the absence of polyglandular disease.

The formation of an immune complex may be detected in any of a number of ways. In one embodiment, a detectably labeled CYP17 protein is provided. Alternately, the immune complex may be detected by forming a second immune complex between the anti-CYP17 autoantibody and a detectably labeled secondary antibody that binds immunoglobulin, preferably the immunoglobulin backbone of the autoantibody. In another embodiment, the autoantibody is detected by formation of an immune complex with a detectably labeled anti-idiotype antibody that specifically recognizes the complementarity determining region (CYP17-binding region) of the autoantibody.

The invention further provides a method of diagnosing idiopathic POF or unexplained infertility in an individual, comprising:

(a) contacting the CYP17 protein immobilized on a support with a test sample comprising an anti-CYP17 autoantibody, and (b) determining whether an immune complex forms between the CYP17 protein and the anti-CYP17 autoantibody, wherein the determining is accomplished by contacting the immune complex with a detectably labeled anti-immunoglobulin antibody that recognizes the anti-CYP17 autoantibody. Alternately, this diagnostic method may comprise:

(a) contacting a tissue extract comprising a CYP17 protein with an antibody that is capable of binding the CYP17 protein, then (b) removing immune complexes formed between the CYP17 protein and the antibody that is capable of binding the CYP17 protein, then (c) immobilizing the tissue extract on a solid support, (d) contacting the immobilized tissue extract with a test sample comprising an anti-CYP17 autoantibody, (e) determining whether an immune complex forms between the CYP17 protein and the anti-CYP17 autoantibody, and (f) comparing the amount of immune complex with a control tissue extract that was not contacted with an antibody that is capable of binding a CYP17 protein, wherein the determining is accomplished by contacting the immune complex with a detectably labeled anti-immunoglobulin antibody that recognizes the anti-CYP17 autoantibody.

The reagents may be packaged in the form of a kit containing instructions for using the reagents to diagnose ovarian autoimmunity in an individual having, or suspected of having, idiopathic premature ovarian failure POF or unexplained infertility. These reagents will include a reagent that specifically recognizes an anti-CYP17 CYP17 autoantibody. Such a regeant may include a detectably labeled CYP17 protein or a detectably labeled anti-idiotypic antibody that specifically recognizes the complementarity determining region (CYP17-binding region) of the autoantibody. Preferably, one or more of the reagents are immobilized on a solid support.

DETAILED DESCRIPTION OF THE PREFERRED EMBODIMENTS

Figure 1:
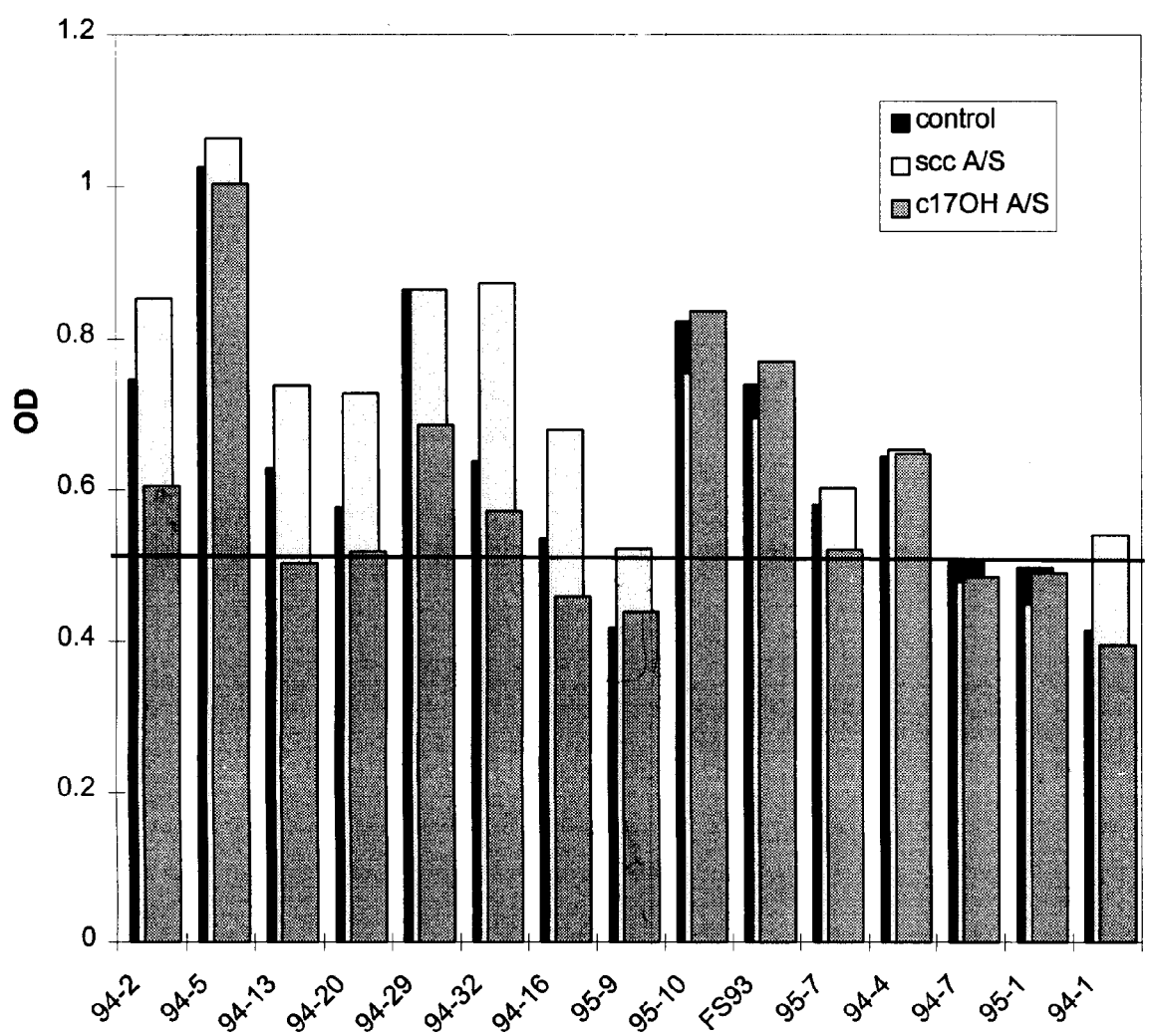
FIG. 1: ELISA assay indicating that sera positive for ovarian autoantibodies contain autoantibodies that recognize CYP17. Optical densities (ODs) above the horizontal line are positive for ovarian autoantibodies. The presence of the indicated antigen is determined by a reduction in the OD relative to the control OD.

The invention provides a method of diagnosing ovarian autoimmunity, comprising the detection of a specific immune complex between a CYP17 protein and an autoantibody. In particular, the invention provides methods for diagnosing ovarian autoimmunity associated with unexplained infertility or idiopathic POF that occurs in the absence of polyglandular disease. The present invention can be used to detect ovarian autoimmunity before the onset of ovarian dysfunction. Thus, the present invention identifies those individuals who would benefit from therapy to maintain, as well as restore, ovarian function. The present invention also informs those individuals with ovarian autoimmunity to bear children before it becomes difficult or impossible due to loss of ovarian function. "Diagnosing", in its various grammatical forms, is herein defined as identifying a disease state, disease progression, or other abnormal condition, based upon symptoms, signs, and other physiological and anatomical parameters.

An immune complex between an anti-CYP17 autoantibody and CYP17 may be detected by any method available to the skilled artisan. An "immune complex" is defined as the non-covalent interaction between an epitope and an epitope-binding region of an immunoglobulin, or a fragment thereof. The art of immune complex detection is highly advanced and may be performed by a number of well-known methods. These methods are reviewed in Coligan et al. (1997) and Hampton et al. (1990), for example.

In one embodiment, immune complexes are detected by the ELISA assay exemplified below. In summary, immune complexes between CYP17 and an anti-CYP17 autoantibody are detected between serum autoantibodies and immobilized rat ovarian tissue. Alternative methods include detection of immune complexes with a radiolabeled CYP17 protein of the invention. Also, autoantibodies may be detected by the use of a labeled anti-idiotypic antibody that specifically recognizes the CYP17-binding site of the autoantibody. Methods of detecting immune complexes are described in greater detail below.

CYP17 is involved in the steroidogenic pathway leading to production of ovarian estrogen. "CYP17 proteins" of the invention may be from any species, and may represent variant or modified forms of CYP17 proteins from various species, provided that the variant or modified CYP17 is capable of forming specific immune complexes with anti-CYP17 autoantibodies from human sera. The variant or modified CYP17 proteins of invention include fragments of CYP17 proteins that are capable of forming specific immune complexes with anti-CYP17 autoantibodies. Methods of isolating CYP17 are well known. Polynucleotides encoding CYP17 also are known in the art, allowing facile production of CYP17, or variants thereof, by recombinant expression. Lund et al. (1998), Chu et al. (1999), Nedelcheva-Kristensen et al. (1999), Lewis et al. (1998), Buczko et al. (1995), Dufau et al. (1997).

Certain preferred embodiments of the invention require the use of antibodies that bind CYP17. These antibodies are distinct from autoantibodies found in POF sera, and they are raised by injecting a host animal with purified CYP17, or an antigenic fragment thereof. The particular source or structure of the anti-CYP17 antibody is not important, provided it specifically recognizes CYP17. Methods of preparing specific antibodies, and methods of preparing antigen binding antibody fragments, or other antigen-binding antibody variants, are well known in the art. For exemplary antibodies against CYP17, see Katulski et al. (1998), Briere et al. (1997), and Belloc et al. (1997).

Under some circumstances, it may be desirable to remove anti-CYP17 autoantibodies from contaminated blood, or products derived from blood. Thus, the invention also provides methods of removing anti-CYP17 autoantibodies in blood from an individual, comprising ex vivo formation of an immune complex between CYP17 and autoantibodies in blood, followed optionally by re-administration of the adsorbed blood. Alternately, immune complexes may be formed in vivo between an anti-CYP17 autoantibody and an antibody that specifically recognizes the CYP17 binding region of an anti-CYP17 autoantibody (an anti-idiotypic antibody). The anti-idiotypic antibody of the invention recognizes the portion of the anti-CYP17 autoantibody that specifically binds CYP17 thereby neutralizing the ability of the autoantibody to interact with its endogenous antigen. The immune complex between the autoantibody and its anti-idiotypic antibody is then cleared naturally by the body. Methods of removing anti-CYP17 autoantibodies are described in greater detail below.

Identification of CYP17 as an Antigen of Ovarian Autoimmunity-Associated Autoantibodies One of the preferred methods of detecting anti-CYP17 autoantibodies is an ELISA developed by the inventor. Representative results of this ELISA are shown in FIG. 1. This ELISA may be used generally to identify specific ovarian antigens of autoantibodies in sera of women with POF or unexplained infertility.

When using whole ovarian tissue as the source of antigens, there is a high correlation (correlation coefficient =0.98; $p<<0.0001$) between results in ELISA tests using rat or human tissue. Because of its greater availability and economy, a rat ovarian tissue extract preferably is used in the ELISA. The cross-reaction of human autoantibodies with rat antigens suggests that there is at least one ovarian antigen that is highly structurally conserved between rat and human. Consistent with this suggestion, rat and human CYP17 are highly evolutionarily conserved, and human autoantibodies thus would be expected to cross-react with rat CYP17.

To detect a given antigen, the antigen is first removed from rat ovarian tissue extract, or "prototype antigen", by precipitation with an antibody that binds the test antigen. Sera from infertile women are then tested for the ability to form immune complexes with the treated or untreated rat ovarian tissue extract. The absence or reduction of a reaction in an antibody-treated sample relative to an untreated, control sample indicates that the antigen responsible for the interaction with the autoantibodies was removed by the pretreatment with the specific antibody.

This assay has the advantage of assessing specific antigens in their native conformation. This avoids possible problems related to the use of recombinant proteins, which may not have the same conformation or carbohydrate content as naturally occurring proteins. For example, an autoantibody that recognizes a three-dimensional determinant of CYP17 (often referred to as a "conformational epitope") may not recognize some recombinantly produced CYP17 proteins if the recombinant proteins are not properly folded.

CYP17 was removed from the rat ovarian tissue extract by adsorption with a specific antiserum, which was provided by Dr. B. Hales (University of Illinois, Chicago). As shown in FIG. 1, most sera from infertile women formed immune complexes with rat ovarian tissue extracts that were pretreated with the control rabbit immunoglobulin (first ten serum samples, from the left, labeled as "control" sera). Positive reactions are indicted by OD values above about 0.53, shown by the horizontal line. Similar results were obtained if these same sera were pretreated with an antiserum that specifically recognizes P450scc ("ssc A/S"). By contrast, six sera pretreated with anti-CYP17 antiserum had significantly lower OD values ("c17OH A/S"). This test indicates that anti-CYP17 autoantibodies are present in six out of ten sera from women with unexplained infertility.

These results would not have been predicted from previous data indicating the virtual absence of CYP17 autoantibodies from POF sera without associated adrenal autoimmunity, discussed above. A speculative hypothesis is that anti-CYP17 autoantibodies were unreactive to the recombinantly engineered proteins used by Chen et al., perhaps because these autoantibodies recognized conformational determinants that were absent in Chen's proteins.

These anti-CYP17 autoantibodies were found in 60% of the sera tested, indicating that the presence of these autoantibodies strongly correlates with ovarian autoimmunity in premature menopause and unexplained infertility. Further, pretreatment of the prototype ovarian antigen with the CYP17 antiserum effectively eliminated the ability of the sera to interact with rat ovarian tissue extract, indicating that anti-CYP17 autoantibodies are a major component of the autoantibodies found in these sera samples.

Preferred Immunoassay Procedures

Screening may be conducted on women with premature menopause, unexplained infertility, and women with poor estrogen response to gonadotropin-induced ovulation. Sera from normally cycling or menopausal women may be used as controls. Screening is not limited to women who manifest ovarian failure and infertility. Screening also may be conducted on women suspected of having an ovarian autoimmune disorder, who may be at an early, preclinical stage of the disorder. Thus, the method of diagnosis of the invention will have value in predicting eventual onset of ovarian dysfunction, allowing afflicted women to plan for treatment or to plan to bear children before the onset of ovarian dysfunction.

Any assay that detects anti-CYP17 autoantibodies will be useful for the practice of the claimed invention. The assay may detect autoantibodies through interaction with a labeled CYP17 protein, for example. Alternatively, the assay may detect autoantibodies indirectly by treating serum that has been pre-adsorbed with antisera specific to a CYP17protein, as described below. Alternately, the assay may detect immune complex formation using labeled anti-idiotypic antibodies that recognize anti-CYP17autoantibodies, described below.

In particular, serological or immunological assays of the invention include, but are not limited to, precipitation, passive agglutination, enzyme-linked immunosorbent assays (ELISA), and radioimmunoassays (RIA). These and other assays are well known in the art. See, e.g., Hampton et al. (1990), Coligan et al. (1997), and Maddox et al. (1983).

In one embodiment of the invention, the components for an immunoassay procedure and instructions for their use are supplied in a kit. Kits can be in solid or liquid phase formats. A preferred kit of the invention includes (i) a CYP17 protein immobilized on a plastic surface and (ii) components for detection of serum antibodies that bind to the immobilized antigen. For example, anti-CYP17 autoantibodies bound to an immobilized CYP17 protein may be detected by adding a labeled secondary antibody that recognizes human immunoglobulin. Alternately, a kit may contain components for precipitating immune complexes that are formed after sera containing autoantibodies is contacted with a CYP17 protein. Immunoprecipitates then would be detected by well-known means. For example, immune complexes between anti-CYP17 autoantibodies and CYP17 may be detected by forming a complex with a labeled anti-CYP17 antibody. The components of this kit are robust, inexpensive, and simple to use. Accordingly, this kit may be useful in remote areas that have no access to modern analytical instrumentation.

Methods of Treatment of Affected Individuals

Individuals testing positive for anti-CYP17 autoantibodies are candidates for treatment with a number of therapeutic approaches. One possible approach is to apply treatments with general applicability to autoimmune disorders, such as immunosuppression with glucocorticosteroids. For a general discussion, see U.S. Pat. No. 5,258,503. General immunosuppressive treatment with steroids may be supplemented by, or replaced by, procedures using immunomodulators, such as cytokines, as described in U.S. Pat. No. 5,888,511, for example.

Another approach is through reproductive endocrinology. Women with POF who do not desire children may choose estrogen replacement therapy. Women desiring a child may undergo a course of immunosuppression, as described in Luborsky et al. (1990). Preferably, treatment is applied after early diagnosis afforded by the inventive diagnostic method, before ovarian autoimmunity has progressed to the point of ovarian failure.

CYP17 Proteins of the Invention

CYP17 proteins are useful for some embodiments of the invention, particularly as an antigen that can be recognized by an anti-CYP17 autoantibody. CYP17 is variously known as 17 alpha-hydroxylase, 17-OH, P450 c17, P450(17 alpha), and 17 alpha-hydroxylase-17,20-lyase. CYP17 is a member of the cytochrome P450 group of enzymes, which is a large superfamily of haemoprotein monooxygenases that play a role in a variety of oxidative metabolic processes. Nebert et al. (1991). One of the many metabolic processes involving P450 enzymes is the steroidogenic hormone pathway, which includes the synthesis of estrogen, androgen, and progesterone in ovarian cells. In adrenal cortical cells, P450 enzymes are involved in glucocorticoid and mineralocorticoid synthesis. In addition to expression in the adrenal and ovary, enzymes catalyzing steroid hormone production also are expressed in testicular and liver tissue. P450 enzymes catalyze side chain cleavage, hydroxylase, dehydrogenase, and aromatase reactions, among others.

CYP17 enzymes themselves are highly conserved enzymes that catalyze the production of DHEA or androstenedione in a series of reactions involving hydroxlase and lyase activities. CYP17 is expressed at low levels in adrenal tissue and at high levels in the ovary, in humans. Dufau et al. (1997).

CYP17 proteins in different species are identified by their close sequence homology, as well as by their shared enzymatic activity. Homology between various species is determined with a two-step multiple alignment procedure set forth in the MULTALIN program of Degtyarenko et al. (1993), incorporated herein by reference. CYP17 has been characterized structurally with great detail, including molecular modeling, as described in Lewis et al. (1998) and Buczko et al. (1995).

In certain embodiments of the invention, anti-CYP17 autoantibodies may be identified by their ability to form immune complexes with a CYP17 protein. A "CYP17 protein" is defined as any CYP17 protein, or fragment or variant thereof, that is capable of forming an immune complex with an anti-CYP17 autoantibody. Generally, fragments or variants of CYP17 will be from about five amino acids in length to about fifty amino acids in length, provided they are antigenic. Preferred antigenic fragments are from five to about twenty amino acids long. Because the usefulness of CYP17 fragments of the invention lies in providing an antigen capable of forming an immune complex with an anti-CYP17 autoantibody, the CYP17 fragments do not necessarily need to exhibit hydroxylase activity.

A CYP17 protein of the invention may be obtained from any of the species where this protein has already been isolated, following procedures known to the skilled artisan. CYP17 proteins from other species may be isolated using similar techniques. Fragments of CYP17 may be made by proteolytic or chemical degradation of isolated CYP17 proteins by well-known methods. Alternately, CYP17 variants and fragments may be prepared by expressing any of the known CYP17-encoding polynucleotides, as described below.

Just as CYP17 can be used to identify sera containing anti-CYP17autoantibodies, positive sera can be used to screen those CYP17 variants or fragments of the invention that are useful in forming immune complexes with anti-CYP17autoantibodies. This screen may be performed by any manner, the artisan can select those herein or by any assay known in the art. In this manner, the artisan can select those variants or fragments that are most expedient for carrying out the methods of the invention. In particular, the artisan thus can avoid using CYP17 proteins that fail to react with anti-CYP17 autoantibodies.

CYP17-Encoding Polynucleotides

Polynucleotides encoding CYP17 also are known in the art. At least the bovine, porcine, rat, and human genes encoding CYP17 proteins have been identified. Lund et al. (1998), Chu et al. (1999), Nedelcheva-Kristensen et al. (1999). The ready availability of CYP17-encoding genes allows recombinant production of CYP17proteins, including variants and fragments of CYP17 by well-established techniques. Representative methods of isolating CYP17-encoding genes and recombinant expression of these genes are described in the art. General methods of manipulating DNA to create fragments and variants of expressed proteins are well known and are reviewed in Sambrook et al. (1989).

CYP17-Binding Antibodies

Antibodies that recognize CYP17 proteins are useful for practicing some embodiments of the invention. The particular source or form of the antibody is not essential for the practice of the invention, provided the antibody specifically binds a CYP17 protein. Although the CYP17 antiserum used for this experiment was from Dr. Hale, any antiserum that specifically recognizes CYP17 can be used. If desired, antibodies against CYP17 proteins may be raised de novo using any of the well-known methods below. Given the high degree of structural relatedness among CYP17, an antibody that recognizes CYP17 from one species is expected to recognize CYP17 from other species.

Antibodies include, but are not limited to polyclonal antibodies, monoclonal antibodies (mAbs), and anti-idiotypic (anti-Id) antibodies. Fragments or derivatives of antibodies include any portion of the antibody that is capable of binding the target antigen or a specific portion thereof. Antibody fragments specifically include, single chain antibodies including single chain Fv (scFv) fragments, Fab fragments, F(ab')$_2$fragments, fragments produced by a Fab expression library, epitope-binding fragments, and humanized forms of any of the above. Affinity of any of these antibodies or fragments for the antigen may be determined by preparing competitive binding curves, as described, for example, in Fisher (1980).

Techniques for preparing polyclonal and monoclonal antibodies as well as hybridomas capable of producing the desired antibody are well known in the art. Campbell (1984), for example. An effective immunization protocol to raise polyclonal antibodies can be found in Vaitukaitis et al. (1971).

An autoantibody paratope that specifically recognizes CYP17 itself may be an epitope for an antibody, a so-called anti-Id antibody. Anti-Id antibodies of the invention, and their paratope-binding fragments, specifically recognize anti-CYP170 autoantibody paratopes and block immune complex formation between the autoantibody and CYP17. Labeled anti-Id antibodies may be useful for detecting anti-CYP17 autoantibodies. Further, anti-Id antibodies may be administered to an individual having anti-CYP17 autoantibodies to prevent undesired immune complex formation between the autoantibody and CYP17. Methods of administering anti-Id antibodies, and methods of promoting their clearance from the body, are described in U.S. Pat. No. 5,958,408, for example. Anti-Id antibodies may be raised against autoantibodies by the techniques described in U.S. Pat. No. 5,227,159, for example.

Having provided purified CYP17 proteins, the invention also provides a means of easily purifying purified anti-CYP17 autoantibodies as an antigen for raising anti-Id antibodies. Anti-CYP17 autoantibodies may be purified by their ability to form immune complexes with a CYP17 protein. For example, the CYP17 protein may be immobilized on a solid support, and serum containing an anti-CYP17 autoantibody may be passed over the support. Anti-CYP17 autoantibodies would be absorbed specifically to the solid support. They then may be eluted from the support using ionic conditions unfavorable for interaction with the CYP17 protein.

Any of the foregoing types antibodies and the like may be immobilized on a solid support, as in immunosorbent assays, for example. Examples of such solid supports include plastics such as polycarbonate, complex carbohydrates such as agarose and sepharose, acrylic resins and such as polyacrylamide and latex beads. Techniques for coupling antibodies to such solid supports are well known in the art. Weir et al. (1986) and Jacoby et al. (1974).

Pathologic Significance of Ovarian Autoantibodies

The pathological significance of autoantibodies in most autoimmune diseases has not been definitively settled. Thus, while autoantibodies are advantageous markers for autoimmune disorders, autoantibodies are not necessarily causal factors in disease progression. In the case of ovarian autoimmunity, the significance of ovarian autoantibodies as a causal component of ovarian disorder has not been completely elucidated. For example, ovarian autoantibodies may develop as a secondary manifestation of pathogenesis that leads to release of ovarian proteins. Luborsky et al. (1999a).

However, autoantibodies themselves may be deleterious under certain circumstances. For example, autoantibodies that bind ovarian proteins on the cell surface may lead to cellular destruction through fixation of complement. Significantly, ovarian autoantibody-positive sera have been shown to participate in complement-dependent cell lysis (shown in 9 of 9 POF sera tested, and in 0 of 4control sera). CYP17 is an intracellular protein, but it is known to be associated with the endoplasmic reticulum. There is some suggestion that ER-associated proteins may also be present on the cell surface (plasma membrane) because the ER and the cell surface are contiguous. For example, thyroid peroxidase, a major, diagnostic antigen in thyroid autoimmune disease, was found to be expressed on the cell surface, as well as in the cytoplasm. Guo et al. (1997), Chiovato et al. (1994). CYP17 likewise may be exposed on the cell surface, where it may interact with anti-CYP17 autoantibodies to promote ovarian disease.

Further, ovarian autoantibodies may aggravate or cause other pathologies. For example, the reaction of autoantibodies with ligands in serum may lead to deposition of ligand/autoantibody complexes in the glomerulus and capillary beds, which may lead to serious disease states. U.S. Pat. No. 5,258,503.

Accordingly, the removal of ovarian autoantibodies is expected to be of therapeutic value. Plasma exchange has been successfully used to remove autoantibodies from the circulation. Other methods and apparatuses for removal of autoantibodies from circulation are known in the art. U.S. Pat. No. 5,258,503 for example, describes a method of ex vivo treatment of blood of an affected individual known as plasmaphoresis. Efficacy of this method is greatly enhanced by possession of antigens specifically recognized by the autoantibody that is being removed. In this instance, blood is passed over an insoluble support to which the antigen is immobilized. Autoantibodies are removed specifically by forming an immune complex with the immobilized antigen.

This method, and other similar methods known in the art, is applicable to removal of the anti-CYP17 autoantibodies using the CYP17 proteins of the invention. For example, serum of an individual harboring anti-CYP17 autoantibodies is treated ex vivo with an immobilized CYP17 protein, or variant or fragment of a CYP17 protein. The autoantibodies are specifically removed from the bodily fluid, which is then re-administered to the individual.

Alternately, an anti-idiotypic antibody is administered to a bodily fluid of an individual with anti-CYP17 autoantibodies. The anti-idiotypic antibody of the invention specifically recognizes the portion of the anti-CYP17 autoantibody that specifically binds a CYP17 protein, thereby neutralizing the ability of the autoantibody to interact with its endogenous antigen. The immune complex between the autoantibody and its anti-idiotypic antibody is then cleared naturally by the body. Methods of using anti-Id antibodies therapeutically and modifying anti-Id antibodies to assist clearance are known in the art. Briefly, an anti-Id antibody may be raised against an isolated anti-CYP17 autoantibody that is injected into an animal, for example. Anti-Id antibodies raised against the anti-CYP17 autoantibody will be directed against the CYP17-binding region of the autoantibody.

The present invention, thus generally described, will be understood more readily by reference to the following examples, which are provided by way of illustration and are not limiting of the present invention.

EXAMPLE 1

This example demonstrates the presence of ovarian autoantibodies that recognize CYP17 in sera from women with unexplained infertility. As shown in FIG. 1, an ELISA assay was performed with 10 sera positive for ovarian antibodies (sera 94-2 through 95-7, from left to right on the X-axis of FIG. 1) and 5 sera negative for ovarian antibodies (sera 94-4 through 94-1). Rat ovarian tissue extract is used as a source of ovarian antigens. This tissue extract first is preadsorbed by passing it over an affinity matrix containing either bound control rabbit serum immunoglobulin, antisera against P450scc, or antisera against CYP17. Each preadsorbed antigen extract was used in a separate ELISA with the panel of sera indicated. Reduction of the test signal indicates a specific reaction requirement for the subtracted antigen. Optical density values above the horizontal line are positive for an interaction between an ovarian autoantibody and its specific antigen in the test sera.

In detail, rat ovarian tissue homogenate was thawed and rinsed with wash buffer [10 mM phosphate buffer, pH 7.4, 30 mM NaCl, 1 mM $MgCl_2$, and 0.01% thimersol (Pierce Chemical Co., Rockford, Ill.)]. Tissue was then homogenized and centrifuged at 1000×g for 15 min to remove debris and nuclei. The supernatant was then centrifuged again at 10,000×g for 30 min. The pellet was resuspended in the same buffer to a concentration of 10 mg/ml (wet weight equivalent). The supernatant was diluted to 0.1 μmg protein/0.1 ml and bound to an ELISA plate.

Autoantibody/antigen complex formation was detected between patients' sera and the ovarian antigen that was immobilized on the ELISA plate. Whole serum was diluted to 1:100 or 1:200 in Tris buffer (pH 7.4) containing 1% BSA and 0.05% Triton X-100. In order to determine whether test signal was due to P450 scc or CYP17, the ovarian antigen (10,000×g pellet) was adsorbed with an affinity matrix (Agarose-protein A/G, Sigma Chemical Company) bound to either normal rabbit serum immnunoglobulins (control), P450 scc antibodies or CYP17 antibodies to remove the corresponding antigen from the crude ovarian antigen. Each antigen was then coated with on ELISA plates and tested against the same panel of serum from unexplained infertility patients.

A routine ELISA procedure was used, as described by Voller et al. (1986). All ELISA assays were carried out in a moisture box. Between each incubation, plate wells were washed three times in Tris-buffered wash solution containing 0.05% Triton X-100. Typical ELISA plates were 96-well polystyrene assay plates (Immulon 4, Dynatech Laboratories, Inc., Alexandria, Va.). Plates are stored frozen at −80° C., before use.

ELISA plates were coated by the addition of 0.1 ml of the treated rat ovarian antigen extract to the wells (2 h at 22° C.). After antigen coating, excess homogenate was removed, and non-specific sites were blocked with 3% BSA in wash buffer (0.15 ml for 16 h at 4° C.). Wells were incubated with test sera (0.1 ml for 1.5–2 h at 22° C.). Goat anti-human immunoglobulin (H-plus L-chain immunoglobulin, G-specific) conjugated to alkaline phosphatase (Sigma Chemical Corporation or ICN, Irvine, Calif.) was then added (0.05 ml for 2 h at 22° C.). Wells were washed twice with wash buffer, and four times with glass-distilled water (0.2 ml each). Alkaline phosphatase was developed with AP substrate (Sigma Chemical Co., St. Louis, Mo.; 0.24 mM $MgCl_2$ in 1 M diethanolamine adjusted to pH 9.8 containing 1 mg/ml p-nitrophenylphosphate as substrate). The plates were read in an ELISA Plate Reader (Molecular Devices ThermoMax Reader) at 405 nm. The results are shown in FIG. 1.

Partial or total signal reduction was observed in 6 of 10 infertility sera after CYP17 was adsorbed from the prototype ovarian antigen. Adsorption of the rat ovarian antigen with antiserum to P450 scc had no effect on the ELISA signal. The five sera that were negative controls showed no change when adsorbed with antisera against P450 scc or CYP17. This provides evidence that one of the antigens to the autoantibodies in infertility sera is CYP17. This assay reveals CYP17 as a major antigen present in a majority of infertile sera. These results also suggest the presence of additional, unidentified antigens in these sera.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

BIBLIOGRAPHY

Arif et al. (1996) *J. Clin. Endocrinol. Metab.* 81(12): 4439–4445.
Barbarino-Monnier et al. (1991) *Fertil. Steril.* 56:928–932.
Belloc et al. (1997) *Pharmacogenetics.* 7:181–186.
Briere et al. (1997) *J. Histochem. Cytochem.* 45:1409–1416.
Buczko et al. (1995) *J. Steroid Biochem. Mol. Biol.* 52:209–213.
Campbell (1984) Monoclonal Antibody Technology: Laboratory Techniques in Biochemistry and Molecular Biology, Elsevier Science Publishers, Amsterdam, The Netherlands.
Chen et al. (1996) *J. Clin. Endocrinol. Metab.* 81(5): 1871–1876.
Chiovato et al. (1994) *J. Clin. Endocrin. Metab* 79:653–656.
Chu et al. (1999) *Endocrinology.* 140:632–640.
Coligan et al. (1997 and periodic supplements) Current Protocols in Immunology, Greene Pub. Associates and Wiley–Interscience, New York, N.Y.
Coulam et al. (1983) *Semin. Reprod. Endocrinol.* 1:161–167.
Degtyarenko et al. (1993) *FEBS Lett.* 332:1–8.
Dufau et al. (1997) *Steroids.* 62:128–132.
Farhi et al. (1997) *Human Reprod.* 12:241–243.
Fisher (1980) Chap. 42 In: Manual of Clinical Immunology, 2d ed., Rose et al., eds., Amer. Soc. Microbiology, Washington, D.C.
Forti et al. (1998) *J. Clin. Endocrinol. Metab.* 83:4177–4188.
Gobert et al. (1992) *J. Reprod. Fertil.* 96:213–218.
Guo et al. (1997) *Clin. Immunol. Immnunopathol.* 82:157–162.
Hampton et al. (1990) In: Serological Methods, a Laboratory Manual, APS Press, St. Paul, Minn., Section IV.
Hoek et al. (1997) *Endocrin. Rev.* 18(1): 107–134.
Jacoby et al. (1974) *Meth. Enzym.* 34 Academic Press, N.Y.
Katulski et al. (1998) *Endocrinol. Invest.* 21:304–309.
Lewis et al. (1998) *J. Steroid Biochem. Mol. Biol.* 66:217–233.
Luborsky et al. (1990) *J. Clin. Endocrinol. Metab.* 70:69–75.
Luborsky et al. (1998) *The XIIth Ovarian Workshop (Serono Symposia)*, Houston, Tex., August.
Luborsky et al. (1999 a) *Clinical Immunol.* 90:368–374.
Luborsky et al. (1999 b) "Ovarian antibodies, FSH and inhibin: independent markers associated with unexplained infertility." Manuscript in preparation.
Luborsky et al. (1999 c) *J. Reprod. Immunol.* 42:79–84.
Lund et al. (1998) *Endocrin. Res.* 24:497–504.
MacCorkle et al. (1999) Submitted to ASRM Meeting.
Maddox et al. (1983) *J. Exp. Med.* 158:1211–1216.
McKenna et al. (1999) *AAAS*, San Diego, Calif.
Meyer et al. (1990) *Obstet. Gynecol.* 75:795–799.
Nebert et al. (1991) *DNA Cell Biol.* 10:1–14.
Nedelcheva-Kristensen et al. (1999) *Cancer Res.* 59:2825–2828.
Roitt (1994) In: Essential Immunology. Blackwell Scientific, Boston, Mass., pp 383–428.
Sambrook et al. (1989) Molecular Cloning: A Laboratory Manual, 2d ed., Cold Spring Harbor Laboratory Press, Cold Spring Harbor, N.Y.
Tung (1995b) *Hormone Metabolic Research.* 27(12): 539–543.
Tung et al. (1995a) *Human Reproduction Update.* 1(1): 35–50.
Vaitukaitis et al., (1971) *J. Clin. Endocrinol. Metab.* 33:988–991.
Voller et al. (1986) In: Manual of Clinical Laboratory Immunology, Rose et al., eds., American Society for Microbiology, Washington, D.C. Pages 99–109.
Weir et al. (1986) Handbook of Experimental Immunology, 4 th Ed., Blackwell Scientific Publications, Oxford, England, Chapter 10.

What is claimed is:

1. A method for determining ovarian autoimmune responses in a female patient having, suspected of having or suspected of having a predisposition for premature ovarian failure or unexplained infertility in an absence of polyglandular disease, comprising:

(a) contacting a sample from the patient with an isolated steroid 17-alpha-hydroxylase (CYP17) protein; and (b) detecting formation of an immune complex between any anti-CYP17 autoantibody present in the sample and the isolated CYP17 protein, wherein detection of the immune complex indicates that the patient has an autoimmune response indicative of the presence of or predisposition for premature ovarian failure or infertility in the patient and wherein the premature ovarian failure or unexplained infertility occurs in the absence of polyglandular disease.

2. The method of claim 1, wherein the patient manifests premature ovarian failure or unexplained infertility.

3. The method of claim 1, wherein the patient does not manifest ovarian failure or unexplained infertility.

4. The method of claim 1, wherein the patient is human.

5. The method of claim 1, wherein the sample is serum.

6. The method of claim 1, wherein the CYP17 protein is detectably labeled.

7. The method of claim 1, wherein the immune complex is detected by forming a second immune complex between the anti-CYP17 autoantibody and a detectably labeled antibody the binds the autoantibody.

8. A method for determining ovarian autoimmune responses in a female patient having, suspected of having or suspected of having a predisposition for premature ovarian failure or unexplained infertility in an absence of polyglandular disease, comprising:

(a) providing isolated steroid 17-alpha hydroxlase (CYP17) protein immobilized on a solid support.

(b) contacting the solid support with a test sample from the patient; and (c) detecting formation of an immobilized immune complex between the isolated CYP17 protein on the solid support and any anti-CYP17 autoantibody present in the sample, said detecting being accomplished by contacting the contacted solid support with a detectably labeled anti-immunoglobulin antibody that recognizes and binds to the anti-CYP17 autoantibody and detecting label bound to the solid support, wherein detection of the formation of the immune complex indicates that the patient has an autoimmune response indicative of the presence of or predisposition for premature ovarian failure or infertility in the patient and further wherein the premature ovarian failure or unexplained infertility occurs in the absence of polyglandular disease.

9. A method for determining ovarian autoimmune responses in a female patient having, suspected of having or suspected of having a predisposition for premature ovarian failure or unexplained infertility, comprising:

(a) providing a tissue extract comprising steroid 17-alpha hydroxylase (CYP17) protein, (b) treating a portion of the tissue extract with an antibody that specifically binds CYP17 to form an immune complex between the anti-CYP17 antibody and the CYP17 protein and removing the immune complex from the extract to provide a CYP17-depleted tissue extract, (c) immobilizing the tissue extract and the CYP17-depleted tissue extract on separate solid supports to provide first and second solid supports, respectively, (d) contacting the first solid support with a portion of a test sample from the patient and detecting formation of an amount of immobilized first immune complex between the tissue extract on the first solid support and any autoantibody present in the sample, said detecting being accomplished by contacting the contacted first solid support with a detectably labeled anti-immunoglobulin antibody that recognizes and binds to the autoantibody and detecting label bound to the first solid support, (e) contacting the second solid support with another portion of the test sample from the patient and detecting formation of an amount of immobilized second immune complex between the CYP17-depleted tissue extract on the second solid support and any autoantibody present in the sample, said detecting being accomplished by contacting the contacted second solid support with the detectably labeled anti-immunoglobulin antibody that recognizes and binds to the autoantibody and detecting label bound to the second solid support, (f) comparing the detected amounts of the immobilized first immune complex and the immobilized second immune complex, wherein a lower detected amount of the immobilized second immune complex compared to the amount of immobilized first immune complex detected indicates that the patient has an autoimmune response against CYP17 indicative of the presence of or predisposition for premature ovarian failure or infertility in the patient.

* * * * *

UNITED STATES PATENT AND TRADEMARK OFFICE
CERTIFICATE OF CORRECTION

PATENT NO. : 6,458,550 B1
DATED : October 1, 2002
INVENTOR(S) : Judith L. Luborsky It is certified that error appears in the above-identified patent and that said Letters Patent is hereby corrected as shown below:

<u>Column 1,</u>
Line 3, insert --    STATEMENT OF GOVERNMENT RIGHTS
      This invention was made with United States government support awarded by the following agency: National Institute of Health: 1-R41-HD34291-01. The United States has certain rights in this invention. --

Signed and Sealed this

First Day of June, 2004

JON W. DUDAS
*Acting Director of the United States Patent and Trademark Office*